United States Patent
Kovi et al.

(10) Patent No.: US 10,464,888 B2
(45) Date of Patent: *Nov. 5, 2019

(54) PROCESS FOR THE PREPARATION OF ISOSULFAN BLUE

(71) Applicant: Apicore US LLC, Canonsburg, PA (US)

(72) Inventors: Ravishanker Kovi, Monroe, NJ (US); Satyam Nampalli, Hunt Valley, MD (US); Peter Xavier Tharial, Edison, NJ (US)

(73) Assignee: Apicore US LLC, Canonsburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,021

(22) Filed: Feb. 1, 2019

(65) Prior Publication Data

US 2019/0177269 A1    Jun. 13, 2019

Related U.S. Application Data

(63) Continuation of application No. 16/170,510, filed on Oct. 25, 2018, which is a continuation of application No. 15/801,585, filed on Nov. 2, 2017, which is a continuation of application No. 15/095,791, filed on Apr. 11, 2016, now abandoned, which is a continuation of application No. 13/310,019, filed on Dec. 2, 2011, now Pat. No. 9,353,050, which is a continuation of application No. 12/643,056, filed on Dec. 21, 2009, now abandoned, which is a continuation of application No. 12/180,057, filed on Jul. 25, 2008, now Pat. No. 7,662,992, which is a continuation of application No. 11/747,291, filed on May 11, 2007, now abandoned.

(51) Int. Cl.
| | | |
|---|---|---|
| *C07C 309/46* | (2006.01) | |
| *C07C 303/22* | (2006.01) | |
| *C07C 303/02* | (2006.01) | |

(52) U.S. Cl.
CPC .......... *C07C 309/46* (2013.01); *C07C 303/02* (2013.01); *C07C 303/22* (2013.01)

(58) Field of Classification Search
CPC .... C07C 303/02; C07C 303/22; C07C 309/46
See application file for complete search history.

(56) References Cited

U.S. PATENT DOCUMENTS

| | | |
|---|---|---|
| 1,531,507 A | 3/1925 | Rosenbaum |
| 1,805,925 A | 5/1931 | Schmidt |
| 1,878,530 A | 9/1932 | Kyrides |
| 2,422,445 A | 6/1947 | Stryker |
| 2,726,252 A | 12/1955 | Balon |
| 4,330,476 A | 5/1982 | Hermann |
| 4,710,322 A | 12/1987 | Metz |
| 5,659,053 A * | 8/1997 | Gessner ................. C09B 11/02 552/108 |
| 7,662,992 B2 * | 2/2010 | Kovi .................... C07C 303/22 562/46 |
| 8,969,616 B2 | 3/2015 | Kovi |
| 9,353,050 B2 | 5/2016 | Kovi |
| 2006/0224003 A1 | 10/2006 | Kulkarni |
| 2008/0281127 A1 | 11/2008 | Kovi |
| 2010/0094044 A1 | 4/2010 | Kovi |
| 2016/0221936 A1 | 8/2016 | Kovi |
| 2018/0057454 A1 | 3/2018 | Kovi |
| 2019/0062268 A1 * | 2/2019 | Kovi .................... C07C 309/46 562/59 |
| 2019/0169119 A1 | 6/2019 | Kovi |
| 2019/0218177 A1 | 7/2019 | Kovi |

OTHER PUBLICATIONS

Rodd's Chemistry of Carbon Compounds by S. Coffey, 1974 2nd Edition vol. III Part F 110-113.
International Search and Written Opinion dated Apr. 23, 2003 of International Application No. PCT/US07/84051.
Office Action for corresponding U.S. Appl. No. 12/180,057 dated Feb. 23, 2009.
Office Action for corresponding U.S. Appl. No. 11/747,291, dated Feb. 7, 2008.
Office Action for corresponding U.S. Appl. No. 12/643,056, dated Jul. 19, 2011.
Coleman et al., "Unexplained Decrease in Measured Oxygen Saturation by Pulse Oximetry Following Injection of Lymphazurin 1% (Isosulfan Blue) During a Lymphatic Mapping Procedure", Journal of Surgical Oncology 1999, 70; 126-129.
Office Action for corresponding U.S. Appl. No. 13/310,019, dated Jul. 10, 2012.
Office Action for corresponding U.S. Appl. No. 13/951,034, dated Nov. 27, 2013.
Office Action for corresponding U.S. Appl. No. 13/951,034, dated May 23, 2014.
Office Action for corresponding U.S. Appl. No. 15/095,791, dated May 2, 2017.
Dan et al., "1% Lymphazurin vs. 10% Fluorescein for Sentinel Node Mapping in Colorectal Tumors," Arch. Surg., 139, 1180-1184,2004.
Argentine et al., "Strategies for the investigation and control of process-related impurities in drug substances," Advanced Drug Delivery Reviews, 59, 12-28, 2007.
Hiranaka et al., "Chemical Structure and Purity of Dyes Used in Lymphangiograms," Investigative Radiology, 10(1), 79, 1975.

(Continued)

*Primary Examiner* — Clinton A Brooks
*Assistant Examiner* — Kofi Adzamli

(57) ABSTRACT

Isosulfan blue and processes for the preparation thereof are provided. A process is also provided for preparation of the intermediate, 2-chlorobenzaldehyde-5-sulfonic acid, sodium salt of formula (2), used in the preparation thereof and a procedure for the isolation of benzaldehyde-2,5-disulfonic acid, di-sodium salt of the formula (3). Also provided is a process for the preparation of an isoleuco acid of formula (4), which upon oxidation gives rise to isosulfan blue of pharmaceutical grade which can be used for preparation of pharmaceutical formulations. The isolation and purification procedures provided in the process provide substantially pure isosulfan blue with HPLC purity 99.5% or greater.

22 Claims, No Drawings

(56) References Cited

OTHER PUBLICATIONS

Office Action for corresponding U.S. Appl. No. 16/170,510, dated Jan. 10, 2019.
*Luitpold Pharmaceuticals, INC.* v. *Apicore US LLC*, IPR2018-01640, PTAB Mar. 6, 2019, Paper No. 19.
Peter J. Lee & Alice J. Di Gioia, "Acquity UPLC™ Separation of Triarylmethane Ink Dyes (Part 1)", Waters Corporation, Jun. 2005.
Jerry I. Hirsch et al., "Use of Isosulfan Blue for Identification of Lymphatic Vessels: Experimental and Clinical Evaluation", Am. J. of Roentgenology 139:1061-64, 1982.
Newton et al., "Physiochemical Characteristics of Patent Blue Violet Dye," J. of Pharmaceutical Sciences vol. 70, No. 2, 122-127, Feb. 1981).

\* cited by examiner

PROCESS FOR THE PREPARATION OF ISOSULFAN BLUE

CROSS-REFERENCE TO RELATED APPLICATIONS

This is a continuation application, and claims the benefit, of U.S. patent application Ser. No. 16/170,510, filed Oct. 25, 2018, which is a continuation of U.S. patent application Ser. No. 15/801,585, filed Nov. 2, 2017, which is a continuation of U.S. patent application Ser. No. 15/095,791, filed Apr. 11, 2016, now abandoned, which is a continuation of U.S. patent application Ser. No. 13/310,019, filed Dec. 2, 2011, now U.S. Pat. No. 9,353,050, which is a continuation of U.S. patent application Ser. No. 12/643,056, filed Dec. 21, 2009, now abandoned, which is a continuation of U.S. Ser. No. 12/180,057 filed Jul. 25, 2008, now U.S. Pat. No. 7,662,992, which is a continuation of U.S. Ser. No. 11/747,291 filed May 11, 2007, now abandoned, the entireties of which are incorporated herein by reference.

FIELD OF THE INVENTION

The present invention relates to a process for the production of isosulfan blue, and in particular, to a process for the production of isosulfan blue in a substantially pure form.

BACKGROUND OF THE INVENTION

Isosulfan blue, having a chemical name, N-[4-[[4-(diethyl amino) phenyl] (2,5-disulfophenyl) methylene]-2,5-cyclohexadien-1-ylidene]-N-ethylethanaminium, sodium salt and the formula

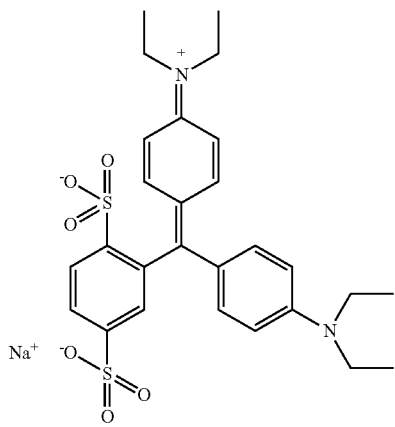

(5)

is a triarylmethane dye used as a contrast agent for the delineation of lymphatic vessels and is particularly useful as a cancer diagnostic agent. Also known chemically as sulfan blue or patent blue, isosulfan blue is an active pharmaceutical ingredient used in the Lymphazurin™ blue dye pharmaceutical dosage form, available as 1% (10 mg/ml) 5 ml solution in phosphate buffer for injection. It is commonly used in a procedure called "mapping of the sentinel lymph nodes". It is an adjunct to lymphography for visualization of the lymphatic system draining the region of injection. It has been used with increasing frequency in localizing sentinel lymph nodes in breast cancer patients. Isosulfan blue-guided surgical removal of cancerous tissue has been on the rise as it is cost effective and safer to use than technetium 99M radioisotope-labeled sulfur colloid. Isosulfan blue is a structural isomer of sulphan blue; both belong to the family of triarylmethane dyestuffs. Generally, preparation of triarylmethane dyes involves condensation of suitably substituted aryl aldehydes with 2 equivalents of alkyl-aryl amines giving rise to leuco-bases or leuco-acids followed by oxidation. Although the literature is replete with methods of preparing triarylmethane dyes, most of the methods involve strong acids for condensation resulting in leuco-bases or leuco-acids, hazardous oxidizing agents (lead oxide, chloranil, iron phthalocyanine/oxone) for converting to triarylmethane dyes, and crude methods (precipitation with sodium sulfate) of purification. See for example U.S. Pat. Nos. 4,330,476, 4,710,322, 1,531,507, 5,659,053, 1,805,925, 2,422,445, 1,878,530 and 2,726,252. Prior art methods of isolation of the crude leuco-acids or leuco-bases involve tedious neutralization/basification with strong bases and typically using the reaction mixtures in the oxidation step, giving rise to crude triarylmethane dyes. The triarylmethane dyestuffs thus prepared are used mainly for dyeing fabric, coloring paper, and printing inks. The literature cites utilization of the same aforementioned synthetic and isolation methods for the preparation of diagnostically important dyes, such as isosulfan blue, sulphan blue and patent blue V. See, Rodd's Chemistry of Carbon Compounds by S. Coffey, 1974 $2^{nd}$ Edition, Volume III Part F, 110-133.

Therefore there is a need in the art for an improved method in the process chemistry of isosulfan blue to be prepared in the purest form which is suitable for large scale cGMP production for its pharmaceutical formulation manufacturing.

SUMMARY OF THE INVENTION

It is therefore an object of the present invention is to provide a simple, safe, cost-effective, time saving and reliable process for the preparation of isosulfan blue in bulk scale and in substantially pure form. "Substantially pure" is defined herein as 99.0% or greater.

Another object of the invention is to provide a simple, cost-effective and reliable process for preparation of the intermediate, 2-chlorobenzaldehyde-5-sulfonic acid, sodium salt of formula (2), required in the preparation of isosulfan blue. This embodiment provides a process step that does not require tedious neutralization with very large quantities of sodium carbonate and effervescence, as is the case in prior art processes.

Another object of the invention is to provide a simplified procedure for the isolation of benzaldehyde-2,5-disulfonic acid, di-sodium salt of the formula (3) that does not include acidifying the reaction mixture with concentrated sulfuric acid and boiling until excess sulfurous acid is expelled, as is taught in the prior art.

Yet another object of the invention is to provide a procedure for obtaining the benzaldehyde-2,5-disulfonic acid, sodium salt of formula (3) free of inorganic salts, which essentially simplifies the isolation procedures to be implemented during isolation of isoleuco acid.

Yet another, object of the invention is to provide a process for the preparation of an isoleuco acid of formula (4), through the urea derivative as an in-situ intermediate. The isoleuco acid of formula (4) on further oxidation gives rise to the target compound, isosulfan blue (5). Still another object of the invention is to use very mild oxidation agent to avoid any over oxidized products and also to improve the stability of the isosulfan blue under reaction conditions.

According to this invention, there is provided a simple procedure for the isolation of benzaldehyde-2,5-disulfonic acid, isoleuco acid and isosulfan blue at acid stage and also at sodium salt formation stage by incorporating crystallization techniques, thereby avoiding distillation and other techniques using high temperatures which jeopardize the compound stability during the manufacturing process.

These and other aspects of the invention will be apparent to those skilled in the art.

DETAILED DESCRIPTION OF THE PREFERRED EMBODIMENTS

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment. In accordance with one embodiment the present invention relates to a process for the preparation of isosulfan blue.

Scheme

The following provides a process for the production of isosulfan blue of formula (5):

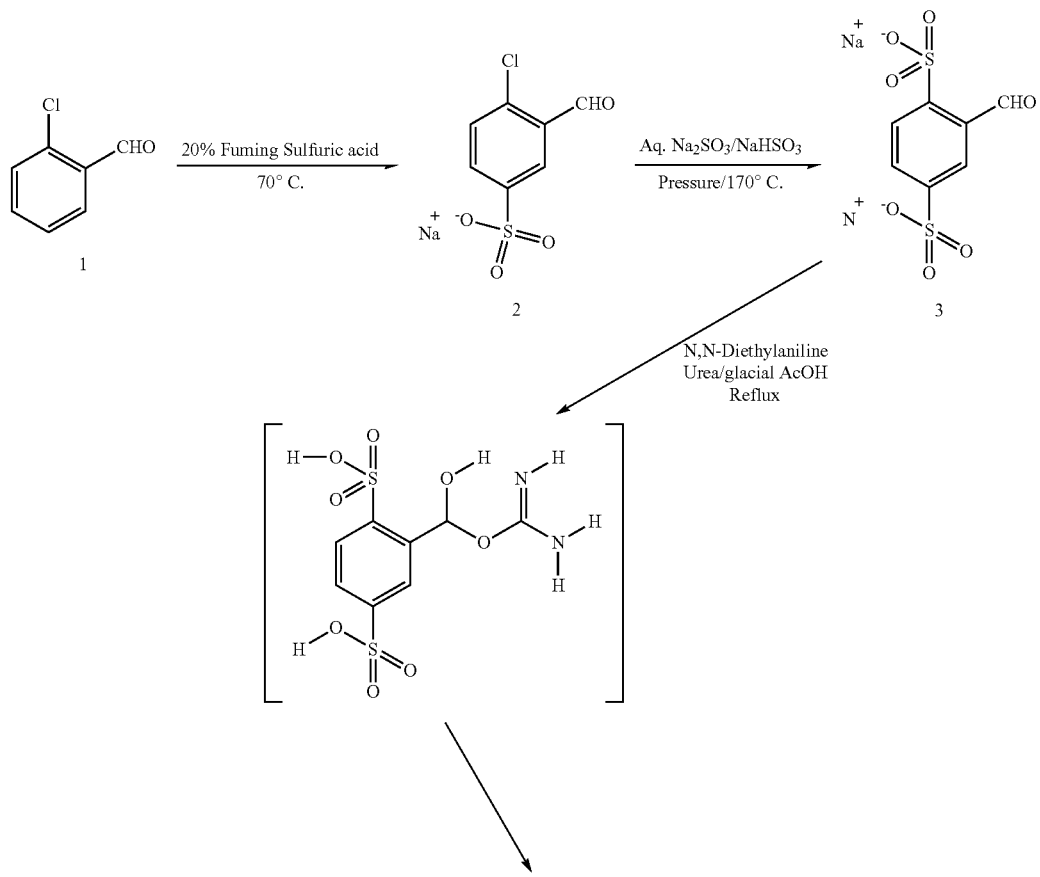

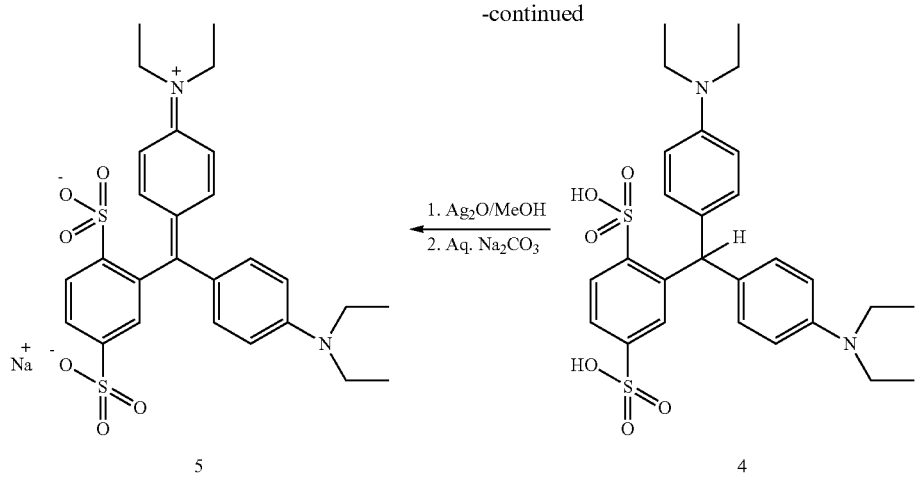

Experimental Procedures

In accordance with one embodiment of the present invention a first step involves sulfonation of the commercially available starting material of the formula (1) to 2-chlorobenzaldehyde-5-sulfonic acid sodium salt of the formula (2).

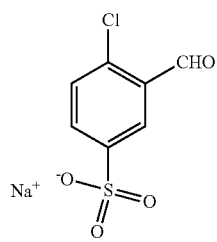

(2)

In one example, the sulfonation process involved reacting one equivalent of the 2-chlorobenzaldehyde of formula (1) with 2.0 equivalents of 20% fuming sulfuric acid at 15° C. to 70° C. for 16 hrs. The reaction mixture was poured into ice-water carefully followed by stirring with solid sodium chloride resulting in a cream colored precipitate, which upon filtration, washing with ether and drying afforded 2-chlorobenzaldehyde-5-sulfonic acid of the formula (2) in 86% yield.

In accordance with one embodiment of the present invention, a second step of the process involves nucleophilic displacement of the chloride in 2-chlorobenzaldehyde-5-sulfonic acid sodium salt of the formula (2) with an alkali metal sulfite/bisulfite such as sodium sulfite/sodium bisulfite at elevated temperatures under closed conditions.

In one example, this reaction was carried out in a Parr pressure vessel equipped with overhead magnetic stirring. 2-Chlorobenzaldehyde-5-sulfonic acid (2), sodium sulfite (2.29 equivalents), sodium bisulfite (10% of sodium sulfite), and water (3.45 mL/g) were charged into the Parr pressure vessel. The reaction mixture in the vessel was stirred and heated at 170-180° C. for 5-7 hours generating 140-150 psi pressure.

The reaction mixture, after cooling, was poured into methanol while stirring, so as to make 20% aqueous content of the whole volume. This process ensured total precipitation of the inorganic salts, which could be removed by filtration. The solvent from the filtrate was removed under reduced pressure to obtain a solid residue, which was triturated with methanol and filtered to afford light yellow colored compound, benzaldehyde-2,5-disulfonic acid, di sodium salt of the formula (3) in 93.9% yield.

In accordance with one embodiment a purification procedure for removing the inorganic salts essentially involves dissolving the crude solid in N, N dimethylformamide and stirring the contents for 1-2 hours at ambient temperature followed by filtration. The filtrate is precipitated by dichloromethane to afford the light yellow colored compound, benzaldehyde-2,5-disulfonic acid disodium salt of formula (3) with chromatographic purity NLT 99.0% and with HPLC assay greater than 90% w/w.

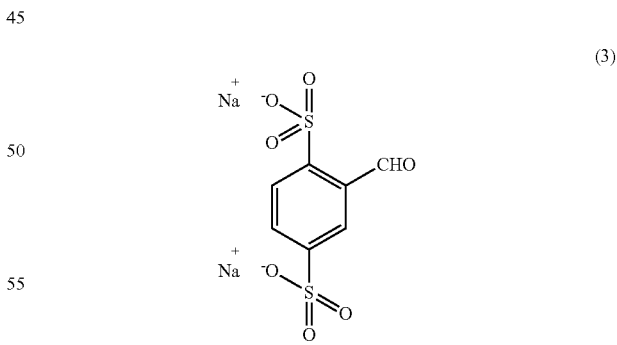

(3)

In accordance with one embodiment of the present invention, a third step of the process involved condensing benzaldehyde-2,5-disulfonic acid, disodium salt of the formula (3) with N, N-diethylaniline to provide isoleuco acid of the formula (4).

(4)

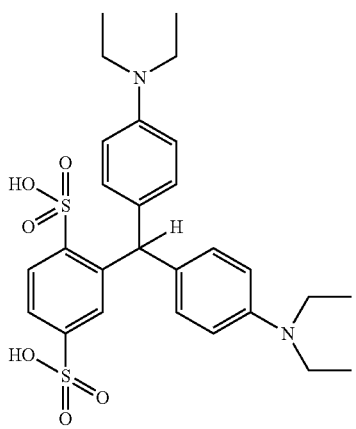

In one example, pure isoleuco-acid of the formula (4) with chromatographic purity greater than 98.0% was obtained in the solid form out of the reaction mixture. A mixture of benzaldehyde-2,5-disulfonic acid, disodium salt of the formula (3), N, N-diethylaniline (2.2 equivalents), and urea (0.75 equivalents) in glacial acetic acid was stirred and refluxed for 20-25 hrs. The reaction progressed through the intermediate formation in-situ which is a urea derivative of benzaldehyde-2,5-disulfonic acid disodium salt. To the above cooled reaction mixture after 20-25 hrs reflux, methanol was added to form a precipitate, which was collected by vacuum filtration and washed with diethyl ether to afford the isoleuco acid of the formula (4) in 56.8% yield.

The purification of isoleuco acid was carried out by dissolving the crude solid in 5 volumes of water and stirred for 1-2 hours at ambient temperature and filtering the solid. The above process was repeated twice before the final solid was washed with acetone to generate isoleuco acid of the formula (4) with chromatographic purity greater than 99.5%.

In accordance with one embodiment of the present invention a fourth step of the process involves conversion of the isoleuco acid (4) to isosulfan blue of the formula (5) under conditions that employ milder oxidizing agents with no strong acidic reagents and are less hazardous than the prior art.

(5)

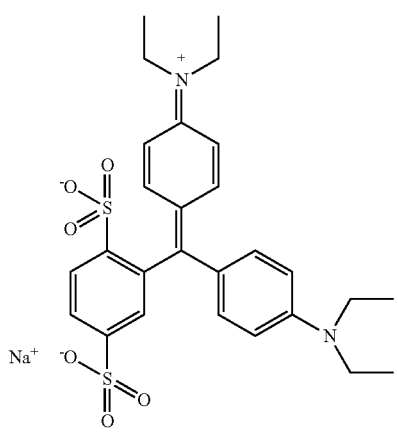

In an example of the present inventive process, a suspension of isoleuco acid of the formula (4) in methanol was stirred at room temperature for 12-14 hrs with silver oxide (2.5 equivalents). The blue colored reaction mixture was filtered through a pad of silica gel and Celite followed by filtration through an acidic zeolite bed and further through a 0.2 micron membrane filtration unit. The filtrate was then precipitated with isopropyl ether at room temperature to obtain crude isosulfan blue acid.

The isosulfan blue acid thus obtained was then purified by recrystallization from aqueous isopropyl alcohol/acetone to afford isosulfan blue acid of chromatographic purity NLT 99.5% performed by High Performance Liquid Chromatography.

The final product of isosulfan blue sodium (formula 5) was obtained when isosulfan blue acid was adjusted to a pH greater than 6.0 in aqueous acetone medium using sodium bicarbonate solution for pH adjustment. The reaction mass was filtered to give isosulfan blue sodium of formula (5) having purity greater than 99.5% by HPLC and also free of silver with silver content estimated by Atomic absorption spectrometer less than 20 ppm.

EXAMPLES

2-Chlorobenzaldehyde-5-Sulfonic Acid, Sodium Salt of the Formula (2)

113.82 g (based on $SO_3$ molecular weight, 569 mL) of 20% fuming sulfuric acid (FSA) was charged into a 1 L three-neck flask fitted with a dropping funnel, overhead stirrer, and thermometer. The reaction mass was cooled to 15 to 20° C. 100 g of 2-chlorobenzaldehyde of the formula (1) was added drop-wise to the stirred and cooled FSA over a period of 40 minutes, so that the temperature didn't rise above 20° C. The reaction mixture was stirred and heated at 70° C. for 16 hours to obtain a dark-brown colored reaction solution. The HPLC results indicated the absence of the starting material. The dark-brown colored reaction solution was carefully poured into a beaker containing 1200 g of crushed ice and stirred. 500 g of solid sodium chloride was added portion wise to the stirred colored acidic solution to precipitate a light-yellow colored solid. The light-yellow colored solid was collected by vacuum filtration and washed with diethyl ether to afford 150.0 g (86.92%) of 2-chlorobenzaldehyde-5-sulfonic acid, sodium salt of the formula (2).

Benzaldehyde-2,5-Disulfonic Acid, Sodium Salt of the Formula (3)

50 g (0.206 mol) of 2-chlorobenzaldehyde-5-sulfonic acid, sodium salt of the formula (2), 59.75 g (0.474 mol, 2.3 eq.) of $Na_2SO_3$ and 5.97 g (10% of $Na_2SO_3$) of $NaHSO_3$ were dissolved in 400 mL of water. The solution was charged into a 600 mL capacity Parr pressure cylinder equipped with stirring and heating. The reaction mixture was stirred (300-310 RPM) and heated at 180° C. (generates ~150 psi pressure) for 5-7 hours. HPLC results indicate the absence of the starting material. After cooling and releasing the pressure, the reaction mixture was poured into 1600 mL of stirred methanol and stirred for 15-30 minutes to precipitate the unwanted inorganic salts. The inorganic salts were filtered off using a pad of Celite and the filtrate evaporated under reduced pressure to obtain a solid residue. The solid residue obtained was triturated with 200 mL methanol, collected by filtration and washed with ether to give 60 g (93.9%) of benzaldehyde-2,5-disulfonic acid, sodium salt of formula (3).

Purification of Benzaldehyde-2,5-Disulfonic Acid, Sodium Salt Formula (3)

60 g of crude benzaldehyde-2,5-disulfonic acid, disodium salt prepared as per the procedure above was dissolved in 500 mL of N, N-dimethylformamide and stirred for 2 hours at 20-25° C. The mixture was filtered through a buchner funnel and the filtrate was precipitated using 1500 mL of dichloromethane to afford 20 g of the light yellow colored compound, benzaldehyde-2,5-disulfonic acid disodium salt of formula (3) with chromatographic purity NLT 99.0% w/w.

Isoleuco Acid of the Formula (4)

60 g of benzaldehyde-2,5-disulfonic acid sodium salt of formula (3), 8.76 g of urea (0.75 eq), and 1000 mL of glacial acetic acid were charged into a 3 L 3-neck flask fitted with a mechanical stirrer and reflux condenser. 65.61 mL (2.2 eq) of N, N-diethyl aniline was added to the stirred mixture and refluxed for 20-25 hrs. When the HPLC results indicated the content of starting material was less than 5%, the reaction mass was cooled to room temperature. After cooling to room temperature, 600 mL of methanol was added and the separated solid collected on a sintered funnel by vacuum filtration. The collected solid was washed with methanol to obtain 55-60 g (56.8%) of crude isoleuco acid of the formula (4).

Purification of Isoleuco Acid of Formula (4)

50 g of crude isoleuco acid along with 250 ml of water was charged into a 1 L 3-neck round bottom flask fitted with a mechanical stirrer. The reaction mixture was stirred for 1 hour at 20-25° C. The solid was filtered through a buchner funnel.

The above process was repeated twice. The final product thus obtained was then washed with 25 ml of acetone and then dried to obtain 40-45 g of the desired isoleuco acid of formula (4).

Isosulfan Blue of the Formula (5)

15 g (0.027 mol) of isoleuco acid of the formula (4) and 225 mL of Methanol were charged into a 1 L round bottomed flask and the suspension was stirred. To the stirred suspension, 15.91 g (0.068 mol, 2.5 eq.) of silver oxide was added in one portion at room temperature and stirred at room temperature for 12-14 hours. The reaction mixture turned blue in color as the oxidation to the desired product progressed. The HPLC results indicated the absence of starting material. The blue colored reaction mixture was filtered through a buchner funnel and the solid silver oxide collected was taken into the reaction flask and the filtrate was kept aside. 225 ml of methanol was added to the silver oxide taken in the reaction flask and stirred at 20-25° C. for 30 minutes and filtered through the buchner funnel. This silver oxide washing procedure with methanol was carried out twice more.

The combined filtrates along with the initial filtrate were then filtered through a bed of silica gel/celite (2 inch silica gel/1 inch of celite) and finally the bed was washed with 50 mL of methanol.

The filtrate was then subjected to a filtration through an acidic zeolite bed of 2 inch height (pH of the zeolite bed was adjusted to acidic pH by using 0.1 N hydrochloric acid aqueous solution) followed by filtration through a 0.2 micron filtration unit.

Isopropyl ether was added three times the volume of the filtrate and the isosulfan blue acid was precipitated as a solid at about 10 gram (68.8%) yield.

In order to prepare the Isosulfan blue sodium salt of the formula (5), 10.0 g of the solid obtained above was dissolved in 30 mL deionized water. Saturated sodium bicarbonate solution was added drop wise to adjust the pH to 8.0. To this 300 mL of acetone was added and stirred at 20-25° C. for 30 minutes. The crystallized product was then filtered through a buchner funnel and the solid thus obtained was dried at 40° C. under vacuum to obtain the isosulfan blue sodium salt of formula (5).

While the preferred embodiments have been described and illustrated it will be understood that changes in details and obvious undisclosed variations might be made without departing from the spirit and principle of the invention and therefore the scope of the invention is not to be construed as limited to the preferred embodiment.

What is claimed is:

1. A process of preparing isosulfan blue acid, said process comprising:

i) combining isoleuco acid of the formula (4):

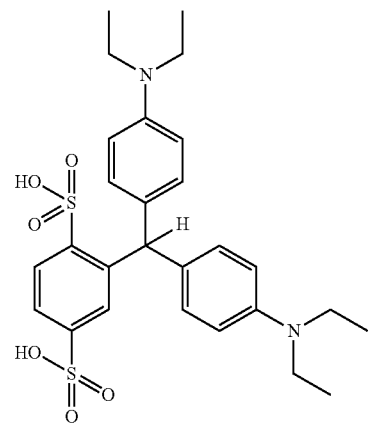

(4)

with a mild oxidizing agent to provide said isosulfan blue acid.

2. The process of claim 1, further comprising the step of recovering said isosulfan blue acid.

3. The process of claim 2, further comprising the step of purifying said recovered isosulfan blue acid.

4. The process of claim 3, wherein said purification comprises recrystallization.

5. The process of claim 4, wherein said recrystallization occurs in a solvent comprising an alcohol.

6. The process of claim 5, wherein said alcohol is aqueous isopropyl alcohol.

7. The process of claim 3, wherein said purification consists of recrystallization.

8. The process of claim 2, wherein said recovery of said isosulfan blue acid occurs by precipitation from solvent.

9. The process of claim 8, wherein said solvent is an ether.

10. The process of claim 9, wherein said ether is isopropyl ether.

11. The process of claim 1, wherein said isoleuco acid is combined with said mild oxidizing agent in the absence of a strong acid.

12. The process of claim 1, wherein said isosulfan blue acid is obtained in a purity of at least 99% as measured by HPLC.

13. The process of claim 12, wherein said isosulfan blue acid is obtained in a purity of at least 99.5% as measured by HPLC.

14. The process of claim 1, wherein said mild oxidizing agent is not lead oxide, chloranil, or iron phthalocyanine/oxone.

15. The process of claim 1, wherein said mild oxidizing agent is silver oxide.

16. The process of claim 1, wherein combining said isoleuco acid of formula (4) with said mild oxidizing agent occurs in a polar solvent.

17. The process of claim 16, wherein said polar solvent is selected from the group consisting of water, alcohol, and mixtures thereof.

18. A process of preparing pharmaceutical grade N-[4-[[4-(diethyl amino) phenyl](2,5-disulfophenyl)methylene]-2,5-cyclohexadien-1-ylidene]-N-ethylethanaminium, sodium salt, said process comprising:
  i) combining isoleuco acid of formula (4):

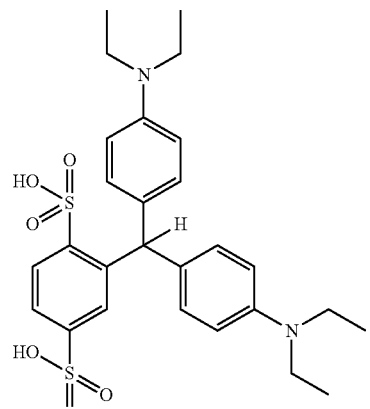

(4)

with a mild oxidizing agent to provide isosulfan blue acid,
  ii) recovering said isosulfan blue acid;
  iii) combining said isosulfan blue acid with a solvent to prepare an isosulfan blue acid mixture; and
  iv) adjusting the pH of said isosulfan blue acid mixture.

19. The process of claim 18, wherein the pH of said isosulfan blue acid mixture is adjusted using a base.

20. The process of claim 19, wherein said isosulfan blue acid mixture is adjusted to a pH greater than 6.0.

21. The process of claim 19, wherein said base is an aqueous carbonate base.

22. The process of claim 21, wherein said aqueous carbonate base is aqueous sodium carbonate.

* * * * *